United States Patent [19]

Boss

[11] Patent Number: 5,843,964

[45] Date of Patent: Dec. 1, 1998

[54] METHODS OF INHIBITING ENDOMETRIAL MITOSES

[75] Inventor: Susan M. Boss, Indianapolis, Ind.

[73] Assignee: Eli Lilly and Company, Indianapolis, Ind.

[21] Appl. No.: 310,292

[22] Filed: Sep. 22, 1994

[51] Int. Cl.$^6$ .............................................. A61K 31/445
[52] U.S. Cl. .......................................................... 514/324
[58] Field of Search ............................................. 514/324

[56] References Cited

U.S. PATENT DOCUMENTS

| | | | |
|---|---|---|---|
| 4,133,814 | 1/1979 | Jones et al. | 546/202 |
| 4,380,635 | 4/1983 | Peters | 546/202 |
| 4,418,068 | 11/1983 | Jones | 546/202 |

FOREIGN PATENT DOCUMENTS

| | | |
|---|---|---|
| WO93/10113 | 5/1993 | Japan . |
| WO93/1074 | 6/1993 | WIPO . |

OTHER PUBLICATIONS

Draper et al., "Effects of Raloxifene (LY139481 HC1) on Biochemical Markers of Bone and Lipid Metabolism i Healthy Postmenopausal Women", Hong Kong, Fourth Int'l Symp. on Osteoporosis, Mar. 29, 1993.

Bryant et al., "Protection from Bone Loss and Lowering of Serum Cholesterol in the Absence of Uterine Stimulation in Ovariectomized Rats", Am Soc. Bone & Min. Res., Tampa, Sep. 18–22, 1993.

Bryant et al., "Raloxifene is a Tissue Specific Estrogen Agonist", Am Soc. Bone & Min. Res., Tampa, Sep. 18–22, 1993.

Frolick et al., "In Vivo and In Virto Metabolism of Raloxifene", Am. Soc. Bone & Min. Res., Tampa, Sep. 18–22, 1993.

Glasebrook et al., "Multiple Binding Sites for the Anti–estrogen Raloxifene", Am Soc. Bone & Min. Res., Tampa, Sep. 18–22, 1993.

Hock et al., "Combination of Raloxifene and Human Parathyoid Hormone 1–34; Increased Femur Bone Mass in Young Ovariectomized (OVX) Rats", Am. Soc. Bone & Min. Res., Tampa, Sep. 18–22, 1993.

Sato et al., "DEXA Analysis of Raloxifene Effects on the Bones From Ovariectomized Rats", Am. Soc. for Bone and Min. Res., Tampa, Sep. 18–22, 1993.

Yang et al., "Raloxifene an Anti–Estrogen, Simulates the Effects of Estrogen in Inhibiting Bone Resorption Through Regulating TGFB–3 Expression in Bone;" .Am Soc. for Bone and Min. Res., Tampa, Sep. 18–22, 1993.

Black et al., "Distinct, Structure–Related Profiles of Estrogenic and Anti–Estrogenic Activity in the Tamoxifen and LY117018 Series;" The Endorcrine Society, Abstract 1982.

Black et al., "Uterine Bioassay of Tamoxifen, Trioxifene, and New Estrogen Antagonist (LY117018) in Rats and Mice," Life Sciences, 26:1980, 1453–1458.

Black et al., "Differential Interaction of Antiestrogens with Cytosol Estrogen Receptors," Molecular and Cellular Endocrinology, 22:1981, 95–103.

Black et al., "Evidence for Biological Action of the Antiestrogens LY117018 and Tamoxifen by Different Mechanisms," Endocrinology 109;1981, 987–989.

Black, L.J. "Biological Actions and Binding Properites of a New Estrogen Antagosist LY117018," In: Homone Antagonist, 129–82, 1982 (M.K. Agarwal ed.) Walter de Gruyter and Co., Berlin New York.

Black et al., LY156758: A Unique Antiestrogen Displaying High Affinity for Estrogen Receptors, Negligible Estrogenic Activity and Near–Total Estrogen Antagonism in Vivo. Presented at the Fifth Anual San Antonio Breast Cancer Symposium, San Antonio, Texas, Nov. 5–6, 1982.

Black et al., The Antiestrogenic Action of LY139481: Species Uniformity Duration of Action and Kinetics of 3H–LY139481 Distribution In Vivo. Sixty–fifth Annual Meeting of the Endocrine Society, San Antonio, Texas, Jun. 8–10, 1983, abs. 93.

Black et al., Antagonism of Estrogen Action with a New benzothiophene Derived Antiestrogen, Life Sciences, 32:1983. 1031–1036.

Black et al., The Relationship of the Antiestrogenic Efficacy of LY156758 to its Pharmacokinetics and Metabolism Following Oral Administration to Adult Ovariectomized Rats, Seventh International Congress of Endocrinology, Quebec City, Canada, Jul. 1–7, 1984, abs. 323.

Black et al., Synthesis and Antiestrogenic Activity of [3,4–Dihydro–2(4–methoxyphenyl)–1–napthalenyl] [4–[2–pyrrolidinyl)ethoxyl]–phenyl] methanone, methanesulfonic acid salt, Journal of Medicinal Chemistry 22;1979, 962–966.

(List continued on next page.)

Primary Examiner—Jerome D. Goldberg
Attorney, Agent, or Firm—James J. Sales; David E. Boone

[57] ABSTRACT

A method of inhibiting endometrial mitoses comprising administering to a human in need thereof an effective amount of a compound having the formula

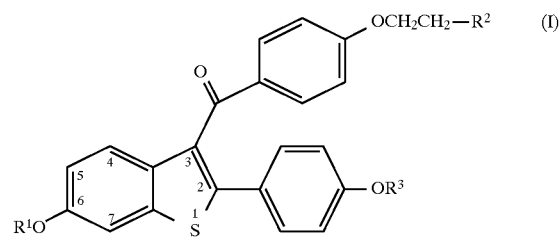

wherein $R^1$ and $R^3$ are independently hydrogen, —$CH_3$,

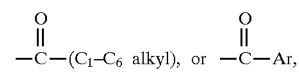

wherein Ar is optionally substituted phenyl;

$R^2$ is selected from the group consisting of pyrrolidine, hexamethyleneamino, and piperidino; or a pharmaceutically acceptable salt of solvate thereof.

4 Claims, No Drawings

OTHER PUBLICATIONS

Black et al., Antiestrogens 2. Structure Activity Studies in a Series of 3–Aroyl–2–arylbenzo[b]thiophene Derivatives Leading to [6–Hydroxy–2–(4–hydroxyphenyl)benzo[b]thien–3–yl] [–[2–(1–piperidinyl)ethoxy]–phenyl]methanone Hydrochloride (LY156758), a Remarkably Effective Estrogen Antagonist with Only Minimal Intrinsic Estrogenicity, J. Med. Chem. 27(8), 1984, 1057–1066.

Gottardis et al., "Contrasting Actions of Tamoxifen on Endometrial and Breast Tumor Growth in the Athymic Mouse", *Cancer Res.,* 48, 812–815, (Feb. 15, 1988).

Gottardis et al., "Effect of Steroidal and Non–Steroidal Antiestrogens on the Growth of a Tamoxifene Stimulated Human Endometrial Carcinoma (EnCalol) in Athymic Mice", *Cancer Res.,* 50, 3189–3192 (Jun. 1, 1990).

Bell et al., "Problematic Uterine Smooth Neoplasms," Am. J. of Surg. Path., 18(6), 535–558 (1194).

Surico et al., "Definition and Classification of Endometrial Carcinoma Precursors," Pan. Med. 29, 229–235, 1987.

Bambone et al., "Pathophysiology and Management of Endometrial Hyperplasia and Carcinoma, " The West J. of Med., 153(1) 50–61 (Jul., 1994).

Silverberg, "Hyperplasia and Carcinoma of the Endometrium," Seminars in Diagnostic Pathology, 5(2), 135–153 (May 1988).

Silva et al., "Malignant Neoplasms of the Uterine Corpus in Patients Treated for Breast Carcinoma: The Effects of Tamoxifene," Intl. J. of Gyn. Path., 13(3), 248–258 (1994).

METHODS OF INHIBITING ENDOMETRIAL MITOSES

BACKGROUND OF THE INVENTION

The uterine lining (endometrium) is composed of tissue, blood vessels, and glands that grow via mitoses when stimulated by the hormone estrogen. In women with normal menstrual cycles, hormonal fluctuations trigger the growth and shedding of the endometrium each month. If conception occurs, the endometrium nourishes the developing embryo.

Most cases of endometrial carcinoma are associated with a precursor lesion termed "endometrial hyperplasia." The classification of endometrial hyperplasia is based on the presence or absence of cytologic atypia, the presence of dysplasia, and the degree of complexity of the architectural pattern. Cytologic atypia is the most predictive criterion for the likelihood of progression to carcinoma.

In simple or cystic hyperplasia with cytologic atypia present there is about an 8% chance of progression to cancer. With complex or adenomatous hyperplasia with cytologic atypia present, there is 29% chance. When no cytologic atypia is present, the progression rate is 1% for simple and 3% for complex hyperplasia.

With continuously elevated estrogen levels, the endometrium remains in its growth phase (mitotic activity) at all time, in some cases leading to an overabundance of endometrial tissue or endometrial hyperplasia. Overgrowth of the endometrium is often a benign condition, but it can also be a precursor of endometrial cancer. Because of this risk, doctors urge women to avoid long-term unopposed estrogen therapy, which can cause endometrial overgrowth if the lining is not continually shed, and to seek prompt treatment for conditions that cause excessive estrogen production. (The use of progesterone in hormone replacement therapy causes breakdown bleeding and shedding of endometrial build up).

Doctors base their treatment decisions on several factors. First, they examine the cells obtained in the biopsy or D&C. If the cells are normal but simply over abundant, future development of cancer is less likely than if the cells are atypical, displaying enlarged nuclei and other unusual features. In some cases, a D&C will show that cancer has already developed. Mitotic activity is also considered.

Endometrial cancer is the most common gynecologic pathology and the fourth most common malignancy in women, after breast, colorectal, and lung cancer. Approximately 30,000–40,000 new cases of endometrial cancer are diagnosed each year. While it is the most common pathology, most patients present in the early stage.

Endometrial cancer affects mainly postmenopausal women, as the average age at diagnosis is 58 years, and fewer than 5% of cases occur prior to age 40. The incidence of endometrial cancer is higher among women with a history of breast, endometrial, or ovarian malignancies, and also in women that belong to a high socioeconomic status.

The most significant risk factors for endometrial cancer are obesity and the presence of estrogen unopposed by progesterone.

The inaccuracy in clinical staging of endometrial carcinoma impedes optimal therapy and analysis of treatment results. Unless metastatic or systemic disease is identified, the initial approach for all medically fit patients is currently a total abdominal hysterectomy/bilateral salpingo-oophorectomy.

Adjunctive therapy, if needed, can be planned, depending on whether the surgical-pathologic findings indicate intrauterine only or extrauterine disease. The patient may receive external beam radiation to the pelvis if pelvic nodes are positive and of external beam radiation to the para-aortic fields if those nodes are positive. Patients with other sites of extrauterine disease may require whole abdominal irradiation. Some patients may need systemic therapy in addition to radiation therapy, depending on sites of spread.

Patients with Stage II disease are at higher risk for having extrauterine disease and recurrence. If the cervix is of normal size and grossly normal, one approach is an extrafascial TAH/BSO with complete surgical staging followed by postoperative irradiation. With gross cervical involvement, two options are available. The first is whole pelvic irradiation followed by one intracavitary implant, which is then followed by a TAH/BSO and para-aortic lymph node sampling. The second option is a radical hysterectomy. BSO, and pelvic and para-aortic lymphadenectomy with irradiation tailored to the surgical findings, if necessary.

In surgical Stage III disease, primary surgery with the use of a TAH/BSO with tumor debulking may be attempted. Extrapelvic disease, depending on the site and extent, may necessitate extended field irradiation, systemic chemotherapy, or hormone therapy. Patients with Stage III disease, by virtue of vaginal or parametrial extension, need a thorough metastatic survey and then irradiation.

Most patients with Stage IV disease are best treated with systemic therapy, which includes hormones or chemotherapy. Pelvic irradiation or hysterectomy is reserved for palliative control purposes.

Patients with recurrent endometrial cancer in the pelvis may be treated with radiotherapy. Unfortunately, the majority of these patients also have distant metastases as well. Isolated central recurrences in the pelvis after irradiation are rare. However, if this situation does occur, selected patients may be candidates for pelvic exenterative surgery. The majority of patients with recurrent disease are treated with hormones or chemotherapy.

Progestins have been used for decades to treat recurrent endometrial cancer. The overall response to progestins is approximately 25%, although recent trials demonstrate lower response rates, in the range of 15 to 20%. Patients with endometrial carcinoma with progesterone-positive and estrogen-positive receptors have a better response to endocrine therapy. Most patients with positive receptors respond to progestins, whereas only 15% with negative receptors respond. Medroxyprogesterone acetate (Provera) and megestrol acetate (Megace) are the agents most commonly used. Tamoxifen (Nolvadex) has also been used to treat patients with recurring endometrial cancer, and responses are usually seen in patients who have previously responded to progestins.

Several cytotoxic agents have activity for endometrial cancer, but responses are short-lived, and the treatment for advanced and recurrent disease is considered palliative. The two most active single agents are doxorubicin and cisplatin. Many combinations of cytotoxic agents have been used, but the results of multiagent chemotherapy do not appear to be significantly better than those of single-agent chemotherapy.

SUMMARY OF THE INVENTION

This invention provides methods of inhibiting endometrial mitoses comprising administering to a human in need thereof an effective amount of a compound of formula I

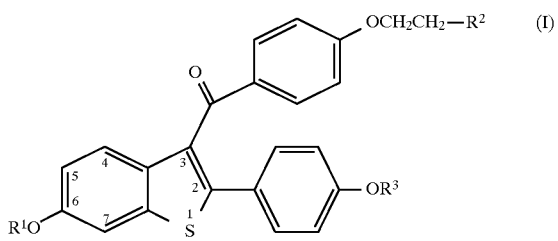

wherein $R^1$ and $R^3$ are independently hydrogen, —$CH_3$,

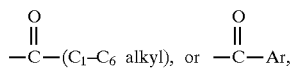

wherein Ar is optionally substituted phenyl;

$R^2$ is selected from the group consisting of pyrrolidino, hexamethyleneimino, and piperidino; and pharmaceutically acceptable salts and solvates thereof.

DETAILED DESCRIPTION OF THE INVENTION

The current invention concerns the discovery that a select group of 2-phenyl-3-aroylbenzothiophenes (benzothiophenes), those of formula I, are useful for inhibiting endometrial mitoses.

The therapeutic and prophylactic treatments provided by this invention are practiced by administering to a human in need thereof a dose of a compound of formula I or a pharmaceutically acceptable salt or solvate thereof, that is effective to inhibit endometrial mitoses.

The term "inhibit" includes its generally accepted meaning which includes prohibiting, preventing, restraining, and slowing, stopping or reversing progression. As such, the present method includes both medical therapeutic and/or prophylactic administration, as appropriate.

Raloxifene is a preferred compound of this invention and it is the hydrochloride salt of a compound of formula 1 wherein $R^1$ and $R^3$ are hydrogen and $R^2$ is 1-piperidinyl.

Generally, at least one compound of formula I is formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like.

The compounds used in the methods of the current invention can be made according to established procedures, such as those detailed in U.S. Pat. Nos. 4,133,814, 4,418, 068, and 4,380,635 all of which are incorporated by reference herein. In general, the process starts with a benzo[b] thiophene having a 6-hydroxyl group and a 2-(4-hydroxyphenyl) group. The starting compound is protected, acylated, and deprotected to form the formula I compounds. Examples of the preparation of such compounds are provided in the U.S. patents discussed above. The term "optionally substituted phenyl" includes phenyl and phenyl substituted once or twice with $C_1$–$C_6$ alkyl, $C_1$–$C_4$ alkoxy, hydroxy, nitro, chloro, fluoro, or tri(chloro or fluoro)methyl.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include ammonium hydroxide, potassium carbonate, methylamine, diethylamine, ethylene diamine and cyclohexylamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I required to inhibit endometrial mitoses according to this invention will depend upon the severity of the condition, the route of administration, and related factors that will be decided by the attending physician. Generally, accepted and effective daily doses will be from about 0.1 to about 1000 mg/day, and more typically from about 50 to about 200 mg/day. Such dosages will be administered to a subject in need thereof from once to about three times each day, or more often as needed, and for a time to effectively inhibit endometrial mitoses.

It is usually preferred to administer a compound of formula I in the form of an acid addition salt, as is customary in the administration of pharmaceuticals bearing a basic group, such as the piperidino ring. For such purposes the following oral dosage forms are available.

Formulations

In the formulations which follow, "Active ingredient" means a compound of formula I.

Formulation 1: Gelatin Capsules

Hard gelatin capsules are prepared using the following:

| Ingredient | Quantity (mg/capsule) |
| --- | --- |
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of specific capsule formulations of raloxifene that have been made include those shown below:

Formulation 2: Raloxifene Capsule

| Ingredient | Quantity (mg/capsule) |
| --- | --- |
| Raloxifene | 1 |
| Starch, NF | 112 |
| Starch flowable powder | 225.3 |
| Silicone fluid 350 centistokes | 1.7 |

Formulation 3: Raloxifene Capsule

| Ingredient | Quantity (mg/capsule) |
| --- | --- |
| Raloxifene | 5 |
| Starch, NF | 108 |
| Starch flowable powder | 225.3 |
| Silicone fluid 350 centistokes | 1.7 |

Formulation 4: Raloxifene Capsule

| Ingredient | Quantity (mg/capsule) |
| --- | --- |
| Raloxifene | 10 |
| Starch, NF | 103 |
| Starch flowable powder | 225.3 |
| Silicone fluid 350 centistokes | 1.7 |

Formulation 5: Raloxifene Capsule

| Ingredient | Quantity (mg/capsule) |
| --- | --- |
| Raloxifene | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

Formulation 6: Tablets

| Ingredient | Quantity (mg/tablet) |
| --- | --- |
| Active ingredient | 0.1–1000 |
| Cellulose, microcrystalline | 0–650 |
| Silicon dioxide, fumed | 0–650 |
| Stearate acid | 0–15 |

The components are blended and compressed to form tablets.

Alternatively, tablets each containing 0.1–1000 mg of Active ingredient are made up as follows:

Formulation 7: Tablets

| Ingredient | Quantity (mg/tablet) |
| --- | --- |
| Active ingredient | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The Active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of Active ingredient per 5 mL dose are made as follows:

Formulation 8: Suspensions

| Ingredient | Quantity (mg/5 ml) |
| --- | --- |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The Active ingredient is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

ASSAY

ASSAY 1

A total of 251 healthy, postmenopausal women are recruited. Each subject has had her last menstrual period more than 6 months but less than 6 years prior to beginning the treatment phase of the study. Postmenopausal status of each subject is confirmed before beginning treatment by serum estradiol <120 pmol/L and by FSH >30 IU/L. Subjects will not have been treated with estrogen over at least the last 3 months before the study and have never been treated with fluoride, calcitonin, or bisphosphonate. Subjects are in good health and range in age from 46 to 60 years.

The study is a multi-center, randomized, controlled, double-blind study. Qualified subjects who consent are randomized to one of four treatment groups: placebo, a compound of formula I 200 mg once daily, a compound of formula I 600 mg once daily, or estrogen 0.625 mg once daily. All subjects also receive daily oral calcium carbonate supplements (520 mg/day elemental calcium). All medications and supplements are taken daily in the morning during the 8-week treatment period. Once treatment is completed (Visit 5), each suject receives Provera® 5 mg/day for 12 days.

Using a Pipelle catheter, a uterine biopsy is performed at baseline and after 8 weeks of treatment. The biopsies are performed in a routine manner and the tissue specimens are placed in 10% buffered formalin. Specimens are retrieved by pouring them into tissue paper filters and then are grossly examined and classified as to appearance (color, texture, and consistency) and volume. Standard histologic processing into paraffin blocks is used and the tissues are serially sectioned onto a minimum of two slides which results in serial strips of 6 to 20 cross sections. Since subjects with clinically significant endometrial abnormalities are to be excluded from the study or are discontinued from the study if they develop abnormalities, the biopsies are evaluated immediately for a descriptive diagnosis. This is performed by one of two pathologists and immediately reported to the clinical physicians. The primary purpose of the biopsies is to determine the degree of morphologic estrogenic effect of study treatment. Two pathologists are trained to read the biopsies by reviewing a series of Pipelle biopsies obtained outside the study that represent the full spectrum of endometrial morphology. Using standard morphologic criteria associated with estrogen-induced proliferation, a scoring system is devised to quantitate this estrogenic effect and include the more subtle changes that may be encountered. Ten of these outside cases are then scored with this system by each pathologist, and the cases are reviewed together to assure uniform understanding and use of the criteria. After the first twenty cases from the baseline biopsies in the study are blindly scored by each pathologist, the scores are reviewed to verify proper use of the system. The pathologists evaluate the biopsy samples for the following components: 1) specimen adequacy, 2) glandular morphology, 3) stromal morphology, and 4) other changes. Additional findings are entered as textual comments. Point scores are generated from the glandular and stromal morphologic features and are totaled and graded on a 4-point estrogenicity scale where a grade of 0 indicates typical postmenopausal endometrium and a grade of 2 indicates a marked estrogenic effect. Total scores for both pathologists are averaged and then assigned a final grade of 0 to 3. Scoring occurs well after the initial immediate diagnosis and usually 10 to 20 cases are scored sequentially.

It is expected that the rate of scant tissue is relatively high on the initial biopsy since the typical postmenopausal endometrium is inactive and consists of a very shallow (5 mm or less) tissue lining and the Pipelle biopsy is a limited, blind biopsy method. Because endometrial glands are required to score features of glandular and stromal morphology, the final biopsy must have contained glands before any conclusions can be drawn in individual subjects. Specimen adequacy is defined as follows:

If no tissue or debatable tissue of endometrial origin is present, the specimen is deemed inadequate and not included in the evaluation.

If multiple fragments of endometrial surface epithelium are obtained, the specimen can not be scored. However the biopsy is deemed adequate and is assigned a grade of 0 on the 4-point scale indicating no estrogen effect.

If disrupted endometrium with glands are obtained, the biopsy is adequate and is scored for the glandular and stromal features.

If intact endometrial tissue is obtained, the biopsy is adequate and is scored for the glandular and stromal changes. In addition, the volume of the tissues is taken into account as an indication of estrogen effect.

Glandular morphology is the primary scoring factor for adequate biopsy specimens. Stromal morphology is the secondary scoring factor for adequate biopsy specimens. Tables 1 and 2 display the features to be used to score each specimen that have glands and/or stroma present. Four features are used to classify the glands: shape, cellular nuclear to cytoplasmic cross sectional areas, nuclear pseudostratification, and mitotic activity.

TABLE 1

Glandular Features: Scoring of Estrogenicity

| Glandular Feature | Estrogenic Effect/Point Value | | |
| --- | --- | --- | --- |
| | No Estrogenicity (0 Points) | Limited Estrogeneicity (1 Point) | High Estrogenicity (2 Points) |
| Shape | Small, tubular straight | Open, straight | Open, cystic, tortuous |
| Nucleus-to-cytoplasm ratio | Very High (>75%) | Moderate (75% to 50%) | Low (<50%) |
| Nuclear pseudostratification | None | Limited | Diffuse |
| Mitoses | None | Rare | Scattered to many |

Note: At least 20 gland profiles are used to grade for mitotic activity (four serial sections of scant specimens).

In more scanty specimens a minimum of 20 gland profiles in serial sections are viewed before concluding no mitoses are evident. In Table 2 the stromal and "other" features are listed. Four features are also used to classify the stroma: density, mitoses, metaplastic changes in epithelia, and tissue volume.

TABLE 2

Stromal Features: Scoring of Estrogenicity

| Stromal Feature | Estrogenic Effect/Point Value | | |
|---|---|---|---|
| | No Estrogenicity (0 Points) | Limited Estrogeneicity (1 Point) | High Estrogenicity (2 Points) |
| Density | Compact, fibrous | Loosely cellular | Edematous |
| Mitoses | None | Rare | Few/Many |
| Metaplasia[a] | None | Rare | Scattered, diffuse |
| Tissue Volume[b] | Disrupted or few intact | Moderate, much being intact | Abundant, intact |

[a]Metaplasia includes tubular, eosinophilic, and squamous type.
[b]Used only if glands show some estrogenic effect (1 or 2 points).

Morphologic features that indicate a lack of estrogenicity generate a score of 0 points and features indicating a limited or significant estrogenic effect generate a score of 1 to 2 points, respectively. Using this approach, a biopsy can receive between 0 to 16 points.

In addition to glandular and stromal morphology, and other important morphologic features including progestational effect, inflammatory processes, breakdown bleeding, polypoid growth, or other pathologic findings are described but are not included in the scoring of proliferative effects since the other changes are primarily nonproliferative.

The sum of the scores obtained from grading the glandular and stromal morphology features result in a 4-point estrogenicity grading scale which is assigned to each sample as follows:

Grade 0=0 to 3 points Typical postmenopausal endometrium with little or no estrogenic effect Grade 1=4 to 6 points Definite but limited estrogenic effect
Grade 2=7 to 10 points Moderte estrogenic effect
Grade 3=>10 points Marked estrogenic effect As noted earlier, if biopsy specimens contain multiple fragments of endometrial surface epithelium, those specimens are assigned a grade of 0.

For each biopsy, there are eight scores: four assessments of the glandular morphology, two assessments of the stromal morphology (density and mitoses scores are combined and metaplasia and tissue volume are combined for statistical analyses), the sum of these six scores and the grade as defined above.

Intraclass correlation coefficients are calculated to assess agreement between the two readers on the sum of the scores obtained at baseline and at 8 weeks (Fleiss, J L (1981) *Statistical Methods for Rates and Proportions.* New York: John Wiley and Sons, p. 218.)

The baseline, week 8 and change-from-baseline to week 8 scores for each of the eight scores are analyzed for treatment differences using Cochran-Mantel-Haenazel statistical techniques adjusting for investigator [Landis, R J Heyman, E R and Koch, G G (1978). "Average Partial Association in Three-Way Contingency Tables: A Review and Discussion of Alternative Tests". International Statistical Review 46:237–254.].

The occurrence of endometrial glands in the biopsy tissue is evaluated at baseline and 8 weeks for treatment differences using the chi-square test.

Pairwise treatment comparisons between each active treatment and placebo are performed if the overall treatment difference is statistically significant. Statistical significance is judged at a two-sided 0.05 level of significance. Al statistical analyses use the SAS system [SAS Institute Inc. (1989), SAS/STAT User's Guide, Version 6, Fourth Edition, Volumes 1 and 2, Cary, N.C.: SAS Institute Inc.]

A positive result in this assay is the reduction of the score for glandular mitoses indicating a decrease in cell replication relative to placebo.

Table 3 illustrates important results of the study.

TABLE 3

Mean (±SEM) Scores for Glandular Features At Endpoint

| Variable | Placebo (n = 53) | Raloxifene 200 mg (n = 54) | Raloxifene 600 mg (n = 54) | Estrogen 0.625 mg (n = 47) |
|---|---|---|---|---|
| Shape | 0.44 ± 0.08 | 0.58 ± 0.07 | 0.51 ± 0.06 | 1.37 ± 0.06* |
| Pseudo-stratifica-tion | 0.64 ± 0.10 | 0.57 ± 0.06 | 0.56 ± 0.06 | 1.68 ± 0.07* |
| Mitoses | 0.19 ± 0.05 | 0.05 ± 0.02* | 0.07 ± 0.03f | 0.98 ± 0.08* |
| Nucleus: Cytoplasm | 0.48 ± 0.09 | 0.58 ± 0.06 | 0.58 ± 0.05 | 1.56 ± 0.08* |

*Statistically significantly different from placebo, two-tailed test (p < .050)
fMarginally significantly different from placebo, two-tailed test (p = .053)

I claim:

1. A method of inhibiting endometrial mitoses comprising administering to a woman in need thereof an effective amount of a compound having the formula wherein $R^1$ and $R^3$ are independently hydrogen, —CH$_3$, $$-\overset{O}{\underset{\|}{C}}-(C_1-C_6 \text{ alkyl}), \text{ or } -\overset{O}{\underset{\|}{C}}-Ar,$$

wherein Ar is optionally substituted phenyl;
$R^2$ is selected from the group consisting of pyrrolidine, hexamethylenemino, and piperidino; or a pharmaceutically acceptable salt of solvate thereof.

2. The method of claim 1 wherein said compound is the hydrochloride salt thereof.

3. The method of claim 1 wherein said administration is prophylactic.

4. The method of claim 1 wherein said compound is or its hydrochloride salt.

* * * * *